United States Patent [19]

Gleason

[11] 4,092,480

[45] May 30, 1978

[54] INTERMEDIATES FOR PREPARING SUBSTITUTED PHENYLGLYCYLCEPHALOSPORINS

[75] Inventor: John Gerald Gleason, Cornwells Heights, Pa.

[73] Assignee: SmithKline Corporation, Philadelphia, Pa.

[21] Appl. No.: 791,810

[22] Filed: Apr. 28, 1977

Related U.S. Application Data

[62] Division of Ser. No. 641,064, Dec. 15, 1975, Pat. No. 4,044,047, which is a division of Ser. No. 384,771, Aug. 1, 1973, Pat. No. 3,953,439.

[51] Int. Cl.$^2$ .................. C07C 101/20; C07C 101/26; A61K 31/54
[52] U.S. Cl. ........................ 560/37; 424/246; 544/26; 560/17; 560/24; 560/29; 560/42
[58] Field of Search ........................... 560/42, 37

[56] References Cited

U.S. PATENT DOCUMENTS

| | | | |
|---|---|---|---|
| 3,464,985 | 8/1969 | Holdrege | 260/243 |
| 3,527,793 | 8/1970 | Holdrege | 560/33 |
| 3,553,258 | 1/1971 | Kaiser et al. | 560/38 |
| 3,634,418 | 1/1972 | Willner | 260/243 C |
| 3,641,021 | 2/1972 | Ryan | 260/243 C |
| 3,682,981 | 8/1972 | Weisenborn et al. | 560/38 |
| 3,860,631 | 1/1975 | Gleason et al. | 560/42 |
| 4,012,382 | 3/1977 | Bouzard et al. | 260/243 C |

OTHER PUBLICATIONS

Chauvette, "Chem. Absts.", vol. 82, 4278(n), 1975.
Gleason et al., "Chem. Absts.", vol. 82, 171435(t), 1975.
Takano et al., "Chem. Absts.", vol. 82, 170993(m), 1975.

*Primary Examiner*—James O. Thomas, Jr.
*Assistant Examiner*—G. T. Breitenstein
*Attorney, Agent, or Firm*—Janice E. Williams; William H. Edgerton; Alan D. Lourie

[57] ABSTRACT

Cephalosporin compounds having a substituted phenylglycyl substituent at the 7-position and any of a variety of groups at the 3-position are prepared by acylation of a 7-aminocephalosporanic acid. The compounds have anti-bacterial activity.

4 Claims, No Drawings

INTERMEDIATES FOR PREPARING SUBSTITUTED PHENYLGLYCYLCEPHALOSPORINS

This is a division of application Ser. No. 641,064 filed Dec. 15, 1975, now U.S. Pat. No. 4,044,047; which is a divisional of Ser. No. 384,771 filed Aug. 1, 1973 now U.S. Pat. No. 3,953,439.

This invention relates to cephalosporin compounds having antibacterial activity. In particular, this invention relates to certain compounds having a substituted phenyl glycyl substituent at position 7 of the cephem nucleus.

The compounds of this invention are represented by the following structural formula:

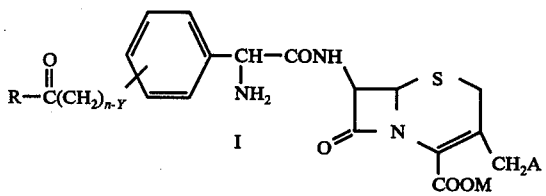

in which:

Y is O, NH or S;

n is one to five;

R is $NH_2$ or OR', where R' is hydrogen or lower alkyl of from one to four carbon atoms;

M is hydrogen or an alkali metal or ammonium cation:

A is hydrogen, acetoxy, pyridyl, SHet, SR' or OR' where R' is hydrogen or alkyl of from one to four carbon atoms; and Het is a five or six-membered heterocyclic group containing carbon and one to four atoms selected from the group consisting of N, O and S, each such group being unsubstituted or substituted with from one to two groups selected from lower alkyl and alkoxyalkyl, each alkoxy or alkyl having from one to four carbon atoms, hydroxy, trifluoromethyl, and SR', where R' is hydrogen or alkyl of from one to four carbon atoms.

Preferred compounds within the scope of the formula I are those where n is one or two and A is hydrogen, acetoxy or SHet. Especially preferred are those were Het is unsubstituted or methyl substituted 1,2,3-triazolyl, 1,2,4-triazolyl, 1,2,3,4-tetrazolyl, oxazolyl, thiazolyl, 1,3,4-oxadiazolyl, 1,3,4-thiadiazolyl, or 1,2,4-thiadiazolyl.

It will be recognized that when the substituent on the heterocyclic group is hydroxy or mercapto, it is possible for the substituent to exist in either of two tautomeric forms, i.e. the oxo or thiono form. The compounds may exist exclusively as one of the two tautomers or may be in equilibrium between the two; however, these are all included within the scope of this invention and the use of one structure or name is intended to indicate both tautomers and mixture thereof.

Cephalosporin derivatives substituted in the 7-position with a phenylglycylacetamido side chain are well documented in the prior art. Amino, alkoxy, and alkylmercapto substitution on the phenyl moiety is described in Belgian Pat. No. 780,021 and Irish Pat. No. 296/64, while lower alkanoylaminophenylglycyl substituents are described in U.S. Pat. Nos. 3,634,418 and 3,464,985. Also disclosed in U.S. Pat. No. 3,634,418, as well as in Irish Pat. No. 296/64, are phenylglycyl groups substituted with various acyloxy groups. Carboxyalkylphenyl and carbamoylphenyl substituents are described in Netherlands Pat. No. 69,02013 and Irish Pat. No. 296/64. Netherlands Pat. No. 69,02013 also discloses phenylglycylcephalosporins with a phenyl group substituted with a carboxamidomethyl group.

Substitution by an S-heterocyclicthiomethyl group at the 3-position of the cephem nucleus is also known in the prior art and is disclosed in, among other patents, U.S. Pat. No. 3,641,021 where Het is methylthiadiazolyl or methyltetrazolyl and Japanese Pat. No. 7124400 where Het is alkyl substituted thiazolyl and tetrazolyl. Although the two last cited patents describe cephalosporins also having a phenylglycylacetamido substituent at the 7-position, the phenyl group is, in both cases, either unsubstituted or substituted with lower alkyl, lower alkoxy, hydroxy, amino, nitro or halogen. U.S. Pat. Nos. 3,516,997 and 3,530,123 also describe 3-S-heterocyclic compounds but with different 7 substituents.

The compounds of this invention are prepared by acylation of a 7-aminocephalosporanic acid with an appropriately substituted phenylglycine. Prior to acylation it is desirable to protect the amino group of the glycine moiety with an easily removable protective group such as t-butoxycarbonyl, benzyloxycarbonyl, trichloroethoxycarbonyl, or similar protective group commonly used in the synthesis of peptides. In most cases, the carboxyl group is activated prior to or during the acylation reaction by conversion to the 2,4-dinitrophenyl or N-hydroxysuccinimidyl ester. If an ester of the carboxyl group on the cephalosporin nucleus is used as an acylation substrate, e.g., a benzhydruyl, t-butyl, trichloroethyl or a benzyl ester, the amine-protected phenylglycine can be coupled directly to the 7-amino group by using a carbodiimide such as dicyclohexylcarbodiimide. Alternatively, the protected phenylglycine can be activated for condensation by reacting it first with carbonyldiimidazole or its equivalent.

Following the acylation, the protective groups can be removed with an acid such as trifluoroacetic acid. The resulting salt is converted to the zwitterionic product by means of a basic ion exchange resin such as polystyrene-amine ion exchange resin (Amberlite IR-45) or else by basification of an aqueous solution of the salt.

The compounds are also prepared by displacement of a 7-acylated 3-acetoxymethylcephalosporin with a mercaptoheterocycle in an aqueous, slightly basic medium.

The suitably blocked substituted phenylglycines are prepared from reaction of an appropriately substituted α-aminophenylacetic acid such as p-amino-D-N-acetylphenyl-glycine (U.S. Pat. No. 3,479,339), and an ω-haloalkanoic acid or acetamide derivative such as α-bromoacetic acid t-butyl ester.

The 7-aminocephalosporins where A is SHet are prepared by known methods from 7-aminocephalosporanic acid (7-ACA) and the appropriate heterocyclic mercapto compound. The compounds where A is hydrogen or acetoxy are prepared by previously known methods from materials known in the art.

The compounds of this invention have antibacterial activity against Gram-positive and Gram-negative organisms. Minimum inhibitory concentrations (MIC's) ranged from 0.4 to >200 μg/ml in in vitro testing. Upon in vivo subcutaneous and oral administration the compounds also showed significant activity. In addition, many of the compounds showed activity against Proteus morgani, an indole-positive bacterium, against which most known cephalosporins and penicillins are inactive. These results are summarized in Tables 1 and 2; compound numbers corresponding to structures are given in the experimental section.

These compounds are formulated and administered by injection in the same manner as other cephalosporins in dosages of from 250 to 1000 mg. Dosage is dependent upon the age and weight of the subject and on the infection being treated and can be determined by those skilled in the art based on the data disclosed herein and experience with known cephalosporins.

the resolved and racemic products obtained from the D & DL-side chains are within the scope of this invention.

Due to the presence of both an amine group and a carboxylic acid group in the cephalosporin compounds of this invention, it is possible, by standard methods, to prepare both acid and base salts of pharmaceutically acceptable nontoxic acids and bases as well as the zwitterionic forms of the compounds. Salts, when obtained, are readily converted to the zwitterions by known methods. It is to be understood that these salts are in-

TABLE 1

In Vitro Activity (MIC)

| Compound No. | S.aureus HH 127 | S.aureus SK 23390 | S.aureus Villalus | Strep. faecalis HH 34358 | E. coli SK 12140 | E.coli HH 33779 | Kleb. pneumo. SK 4200 | Kleb. pneumo. SK 1200 | Sal. paratyphi ATCC 12176 | Shig. paradys HH 112 | Entero. aerog. ATCC 13048 | Proteus morgani 179 |
|---|---|---|---|---|---|---|---|---|---|---|---|---|
| 48536 | 12.5 | 12.5 | 100 | 100 | 3.1 | 6.3 | 1.6 | 3.1 | 1.6 | 3.1 | 12.5 | 12.5 |
| 51436 | 12.5 | 12.5 | 200 | 200 | 25 | 25 | 12.5 | 50 | 12.5 | 25 | 100 | — |
| 99316 | 12.5 | 12.5 | 100 | >200 | 12.5 | 50 | 12.5 | 6.3 | 6.3 | 12.5 | 40 | >200 |
| 08616 | 6.3 | 6.3 | 26 | 100 | 6.3 | 12.5 | 1.6 | 3.1 | 25 | 25 | 25 | 200 |
| 70326 | 6.3,12.5 | 6.3,12.5 | 50,100 | 100,200 | 0.8,1.6 | 1.6,3.1 | 0.4,0.8 | 0.8,0.8 | 0.4,0.8 | 0.4,0.8 | 1.6,3.1 | 6.3 |
| 04726 | 12.5 | 12.5 | 100 | 200 | 25 | 12.5 | 3.1 | 3.1 | 3.1 | 6.3 | 25 | 200 |
| 61726 | 6.3 | 6.3 | 50 | 50 | 12.5 | 25 | 6.3 | 6.3 | 12.5 | 6.3 | 25 | 200 |
| 86526 | 6.3 | 3.1 | 25 | 50 | 25 | 25 | 12.5 | 6.3 | 6.3 | 6.3 | 100 | — |
| 60326 | 12.5 | 12.5 | 200 | 200 | 6.3 | 25 | 6.3 | 6.3 | 3.1 | 6.3 | 25 | >200 |
| *08016 | 50 | 50 | >200 | >200 | 50 | 50 | — | 25 | 25 | 50 | 100 | — |
| 59216 | 6.3 | 25 | 100 | 100 | 6.3 | 12.5 | 3.1 | 6.3 | 6.3 | 6.3 | 12.5 | 200 |
| *59216 | 6.3–25 | 100–200 | 100–100 | 50–200 | 3.1–12.5 | 6.3–25 | 1.6–6.3 | 3.1–12.5 | 3.1–12.5 | 1.6–12.5 | 12.5–50 | — |
| 03326 | 12.5 | 100 | 200 | 200 | 6.3 | 25 | 6.3 | 3.1 | 3.1 | 6.3 | 25 | 200 |
| 42526 | 25 | 25 | 200 | >200 | 6.3 | 12.5 | 3.1 | 3.1 | 6.3 | 6.3 | 12.5 | 100 |
| 07826 | 6.3 | 6.3 | 200 | 100 | 100 | >200 | 100 | 100 | 50 | 50 | >200 | — |
| 26436 | 6.3 | 6.3 | 25 | 50 | 12.5 | 12.5 | 6.3 | 6.3 | 3.1 | 6.3 | 25 | 50 |
| 19736 | 12.5 | 12.5 | 200 | 100 | 50 | 100 | 50 | 50 | 25 | 25 | >200 | >200 |
| 96826 | 3.1 | 3.1 | 25 | 25 | 25 | 50 | 25 | 25 | 25 | 12.5 | 50 | 25 |
| 09036 | 3.1 | 3.1 | 200 | 50 | 25 | 50 | 25 | 25 | 25 | 12.5 | 50 | 25 |
| 71816 | 3.2,12.5 | 1.6,3.1 | 25 | 25 | 6.3 | 12.5 | 3.1 | 6.3,1.6 | 3.1,3.1 | 6.3,3.1 | 12.5,6.3 | 100,200 |
| *71816 | 25 | 12.5 | 100 | 200 | 50 | 50 | 25 | 50 | 12.5 | 12.5 | 100 | — |
| 32626 | 12.5 | 6.3 | 50 | 200 | 12.5 | 25 | 6.3 | 12.5 | 12.6 | 6.3 | 12.5 | 100 |
| 91726 | 6.3 | 6.3 | 50 | 200 | 50 | 25 | 12.5 | 12.5 | 6.3 | 6.3 | 50 | — |
| 96146 | 6.3 | 6.3 | 50 | 25 | 50 | 100 | 50 | 50 | 25 | 25 | 100 | >200 |
| 72546 | 12.5 | 12.5 | 50 | 50 | 25 | 50 | 12.5 | 25 | 12.5 | 12.5 | 50 | >200 |
| 76746 | 6.3 | 6.3 | 50 | 100 | 1.6 | 1.6 | 0.8 | 1.6 | 3.1 | 3.1 | 1.6 | 6.3 |

*Compound with DL side chain, all others D

TABLE 2

| Compound No. | In Vivo Activity ED$_{50}$ (mg/kg) | | | |
|---|---|---|---|---|
| | E.coli 12140 | | Klebs.pneumo. 4200 | |
| | s.c. | p.o. | s.c. | p.o. |
| 99316 | 25.37 | 42.25 | 29.11 | 15.5,15.5 |
| 03616 | 6.2 | 14.5 | 11.5 | 16 |
| 70326 | 2.2 | 11 | 1.7,<3 | 4,3 |
| 04726 | 12.5 | 46 | 9.5 | 14.5 |
| 61726 | — | — | 50 | >50 |
| 86526 | 18 | 42 | 7.2 | 10 |
| 60326 | 11.2 | 200 | 12.5 | 63 |
| 59216 | 9.5 | 25 | 4.8 | 21.5 |
| *59216 | 6.2,9,11 | 50,21.5,40 | 7.2,3,6.2 | 29,22.5,17.6 |
| 03326 | 8.4 | 25 | 4.6 | 17.7 |
| 42526 | 0.5 | >50 | 5.4 | 33 |
| 26436 | 1.2 | 9.6 | 1.5 | 5.5 |
| 19736 | 34 | 25 | — | — |
| 96826 | <3 | 9.4 | 7.2 | 12.5 |
| 71816 | 4.5 | 12.5 | 7.5 | 6.2 |
| *71816 | 13.7 | 21.5 | 11.5 | 13.7 |
| 32626 | 8.7 | >50 | 15.5 | >50 |
| 91726 | 14 | 25 | 12.5 | 13.6 |
| 48536 | 2.0 | 6.4 | 7.8 | 12.5 |
| 96146 | 4.7 | 16 | 2.9 | 17 |

*Compound with DL side chain, all others D

It will be recognized that, due to the asymmetric α-carbon atom in the 7-acetamido group, optical isomers will exist. Racemic or resolved products are obtained, depending upon whether a racemic or resolved phenylglycine side chain is used or upon the reaction conditions used to form the acylated cephalosporin. The resolved side chain acids are readily obtained from the racemic compounds by resolution according to well known methods including fractional crystallization of a salt formed with an optically active acid or base. Both cluded within the scope of this invention.

This invention also consists of the novel intermediate compounds represented by the structural formula:

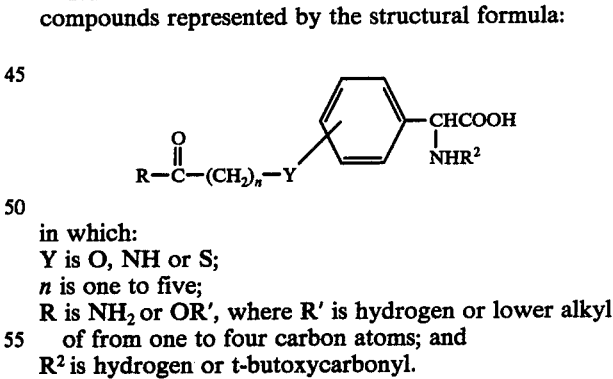

in which:

Y is O, NH or S;

n is one to five;

R is $NH_2$ or $OR'$, where R' is hydrogen or lower alkyl of from one to four carbon atoms; and $R^2$ is hydrogen or t-butoxycarbonyl.

These intermediate compounds are prepared by condensing an N-protected hydroxy, mercapto, or aminophenylglycine ester with a ω-haloalkanoic ester or amide. Removal of protective groups is by standard methods.

The following examples illustrate the invention but are not to be construed as limiting the scope thereof. Temperatures are in degrees Centigrade unless otherwise stated. Each of the products or intermediates obtained as a trifluoroacetate salt is converted to its zwitterion by means of the procedure described in Example 6.

EXAMPLE 1

D-N-t-Butoxycarbonyl-p-t-butoxycarbonylmethylthiophenylglycine p-Amino-D-N-acetylphenylglycine (20.0 g, 0.095 mol) was slowly added to 110 ml (1.4 mol) of trifluoroacetic acid at 5°. The reaction mixture was stirred for 25 minutes, then cooled to −5° and diazotized with a solution of 4.65 g (0.095 mol) of sodium nitrate in 14.5 ml of $H_2O$. The diazonium solution was added to a cold aqueous solution of 58.0 g (1.65 mol) of sodium hydroxide, 28.4 g of sodium sulfide and 3.6 g of sulfur, then left to sit overnight at 25°. Acidification of the reaction mixture to pH2 with conc.HCl gave a gum which was separated, combined with the residue from extraction of the aqueous solution with butanol, and dissolved in 5% sodium bicarbonate. This solution was filtered through Celite to remove excess sulfur, then oxidized with iodine and potassium iodide. Extraction with sodium bisulfite, followed by acidification, gave the crude disulfide, which was recrystallized from methanol-ether (13.8 g, 65%). The product was refluxed in 30 ml of 1:1 dioxane −5% HCl for 14 hours to remove the acetyl protective group. Concentration and crystallization from ethanol-ether gave 11.5 g (63%) amino acid hydrochloride salt. The product (4.37 g, 0.01 mol) was heated at 40°–60° for eight hours with 8.6 g (0.06 mol) of t-butoxycarbonyl azide and 3.2 g (0.8 mol) of magnesium oxide. The reaction mixture was filtered, washed with 5% sodium bicarbonate and the combined filtrate and washings were then extracted with ethyl acetate, acidified to pH2 and re-extracted with ethyl acetate. The extracts were washed with water and saturated NaCl solution; dried ($MgSO_4$) and concentrated in vacuo to give a residue which was crystallized from methylene chloride-hexane (3.5 g, 63%).

The above disulfide (1.5 g; 2.7 mmol) was dissolved in 10 mls of acetone and treated with 2.0 g (5.4 mmol) of tri-n-octylphosphine and 10 ml of 10% methanol in water. The reaction mixture was stirred at 25° for one hour, then it was diluted with 5% sodium bicarbonate solution and extracted with ethyl acetate. The aqueous phase was acidified extracted with methylene chloride and the extracts were washed with water and saturated NaCl solution, dried ($Na_2SO_4$) and concentrated to dryness. The thiol (1 g, 3.5 mmol) was dissolved in 10 ml of ethanol and to this solution was added 1 g (5.1 mmol) of α-bromoacetic acid t-butyl ester and 2.5 g (19 mmol) of diisopropylethylamine. The reaction mixture was stirred for one hour, then extracted with dilute HCl in ethyl acetate. The organic extracts were dried ($Na_2SO_4$) and concentrated to dryness and the residue was chromatographed on silica gel with 99:1 chloroform:acetic acid to give 0.62 g of D-N-t-butoxycarbonyl-p-t-butoxycarbonylmethylthiophenylglycine.

A solution of 0.5 g of D-N-t-butoxycarbonyl-p-t-butoxycarbonylmethylthiophenylglycine in 10 ml of anisole or tetrahydrofuran is treated with trifluoroacetic acid at 0° and stirred for 1.5 hours. The reaction mixture is concentrated in vacuo and the residue triturated with ether to give the D-p-carboxymethylthiophenylglycine salt.

EXAMPLE 2

7-[D-α-Amino-α-(4′-carboxymethylthiophenyl)acetamido]-3-desacetoxycephalosporanic acid (Compound No. 99316)

A mixture of 0.520 g (1.3 mmol) of D-N-t-butoxycarbonyl-p-t-butoxycarbonylmethylthiophenylglycine, 0.425 g (1.9 mmol) of 7-amino-3-desacetoxycephalosporanic acid and 0.330 g (1.6 mmol) of dicyclohexylcarbodiimide in 5 ml of methylene chloride was stirred for 3 hours at 0°. The solvent was removed in vacuo and the residue was shaken with ethyl acetate and 2.5% sulfuric acid. The layers were separated and the organic phase was washed with 5% sodium bicarbonate, water and sodium chloride solution, then dried ($MgSO_4$). Concentration yielded a residue that was dried in vacuo and chromatographed in silica gel with chloroform to give 0.505 g of product. The acid was dissolved in 10 ml of a cold 10% solution of anisole in trifluoroacetic acid and stirred at 0° for 1.25 hours. Concentration in vacuo gave a residue which was triturated with ether and redissolved in a minimum amount of ethanol. Addition of ether to the ethanol solution caused precipitation of the salt.

| Analysis of salt: $C_{18}H_{19}N_3O_6S_2 \cdot \frac{1}{4}CF_3COOH \cdot \frac{1}{2}H_2O$ (503.529) | | |
|---|---|---|
| | Theory | Found |
| C | 45.32 | 45.66 |
| H | 4.00 | 4.30 |
| N | 8.35 | 8.42 |

The salt can be converted to the zwitterionic product by means of a polystyrene-amine ion exchange resin.

EXAMPLE 3

7-Amino-3-(1-methyl-1,2,3,4-tetrazol-5-ylthiomethyl)-3-cephem-4-carboxylic acid To a suspension of 27.2 g (0.1 mol) of 7-ACA in 200 ml of water and 100 ml of acetone was added a solution of 18.9 g of sodium bicarbonate in 200 ml of water. The resultant solution was warmed on a steam bath and a solution of 14.5 & (0.125 mol) of 1-methyl-5-mercapto-1,2,3,4-tetrazole in 200 ml of acetone was added. The reaction mixture was refluxed for 3.5 hours while maintaining the pH at 7.4–8.0 by addition of 5% sodium bicarbonate solution. Acidification of the cooled reaction mixture to pH 3.5 with 6N hydrochloric acid resulted in precipitation of 7-amino-3-(1-methyl-1,2,3,4-tetrazole-5-ylthiomethyl)-3-cephem-4-carboxylic acid which was collected, washed ($H_2O$), and air dried (16 g, 49%).

EXAMPLE 4

7-Amino-3-(5-methyl-1,3,4-thiadiazol-2-ylthiomethyl)-3-cephem-4-carboxylic acid The title compound was obtained from reaction of 7ACA and 5-methyl-2-mercapto-1,3,4-thiadiazole by the same procedure as described in Example 3.

EXAMPLE 5

7-Amino-3-(1,2,3-triazol-4-ylthiomethyl)-3-cephem-4-carboxylic acid

The title compound was obtained from reaction of 7-ACA and 4-mercapto-1,2,3-triazole by the same procedure as described in Example 3.

EXAMPLE 6

7-[D-α-Amino-α-(4'-carboxymethylthiophenyl)acetamido]-3-(5-methyl-1,3,4-thiadiazol-2-ylthiomethyl)-3-cephem-4-carboxylic acid (Compound No. 03616)

A solution of 0.200 g (0.51 mmol) of D-N-t-butoxycarbonyl-p-t-butoxycarbonylemethylthiophenylglycine, 0.214 g (0.53 mmol) of 7-amino-3-(5-methyl-1,3,4-thiadiazol-2-ylthiomethyl)-3-cephem-4-carboxylic acid t-butyl ester, and 0.112 g (0.54 mmol) of dicyclohexylcarbodiimide in 10 ml of methylene chloride was stirred at 0° for 1 hour. The reaction mixture was filtered and the filtrate was washed with 2.5% sulfuric acid, 5% sodium bicarbonate and water, dried (MgSO$_4$) and concentrated to give crude 7-[D-α-t-butoxycarbonylamino-α-(4'-carboxymethylthiophenyl)acetamido]-3-(5-methyl-1,3,4-thiadiazol-2-ylthiomethyl)-3-cephem-4-carboxylic acid, di-t-butyl ester. The ester was dissolved in 10 ml of a 20% solution of anisole in trifluoroacetic acid and stirred at 0° for 1.5 hours. The solvent was removed in vacuo and the residue was triturated with ether. The precipitated trifluoroacetate salt of the title compound was collected, dried in vacuo and recrystallized from ethanol-ether (0.191 g).

Analysis of salt: $C_{21}H_{21}N_5O_6S_4 \cdot \frac{1}{2} CF_3COOH \cdot \frac{1}{2} H_2O$
(633.726)

|   | Theory | Found |
|---|--------|-------|
| C | 41.71  | 41.74 |
| H | 3.58   | 3.79  |
| N | 11.05  | 10.76 |

The trifluoroacetate salt is converted to the zwitterion by stirring an aqueous solution of the salt with a polystyrene-amine ion-exchange resin (Amberlite IR-45) for 1 hour at 25°. The resin is then filtered off and the aqueous solution is lyophilized to yield the zwitterionic cephalosporin which may be converted to the sodium salt by addition of a 30% solution of sodium 2-ethylhexanoate in isopropanol.

EXAMPLE 7

7-[D-α-Amino-α-(4'-carboxymethylthiophenyl)acetamido]-3-(1-methyl-1,2,3,4-tetrazol-5-ylthiomethyl0)-3-cephem-4-carboxylic acid (Compound No. 70326)

The title compound was obtained from reaction of 0.5 g (1.28 mmol) of D-N-t-butoxycarbonyl-p-t-butoxycarbonyl-methylthiophenylglycine, 0.5 g (1.3 mmol) of 7-amino-(1-methyl-1,2,3,4-tetrazol-5-ylthiomethyl)-3-cephem -4-carboxylic acid t-butyl ester, and 0.265 g (1.3 mol) of dicyclohexylcarbodiimide by the same procedures as described in Example 6.

Analysis of zwitterion: $C_{20}H_{21}N_7O_6S_3 \cdot 1 H_2O$
(569.658)

|   | Theory | Found |
|---|--------|-------|
| C | 42.17  | 42.29 |
| H | 4.06   | 4.13  |
| N | 17.21  | 15.41 |

EXAMPLE 8

7-[D-α-Amino-α-(4'-carboxymethylthiophenyl)-acetamido]-3-(1,2,3-triazol-4-ylthiomethyl)-3-cephem-4-carboxylic acid (Compound No. 04726)

A mixture of 1.12 g (2.82 mmol) of D-N-t-butoxycarbonyl-p-t-butoxycarbonylmethylthiophenylglycine, 0.324 g (2.82 mmol) of N-hydroxysuccinimide, and 0.58 g (2.82 mmol) of dicyclohexylcarbodiimide in 20 ml of acetonitrile was stirred at 25° for 12 hours. The reaction mixture was filtered and concentrated to dryness. The residue was then dissolved in ether and the ethereal solution was filtered and concentrated to yield the activated ester as a foam.

A solution of 0.88 g (2.82 mmol) of 7-amino-3-(1,2,3-triazol-4-ylthiomethyl)-3-cephem- 4-carboxylic acid and 0.57 g (5.64 mmol) of triethylamine in 20 ml of dry pyridine was stirred for 0.5 hour. the activated ester from above was then added and the reaction mixture was stirred at 25° for 4.5 hours. Addition of ether to the reaction mixture caused precipitation of the salt which was collected by filtration and dissolved in water. Ethyl acetate was added to the aqueous solution and the mixture was acidified with dilute HCl and filtered. The layers were separated and the organic layer was washed (H$_2$0), treated with activated carbon, dried (MgS0$_4$) and concentrated in vacuo to yield 0.450 g (23%) of product. The deblocked acid was obtained by stirring the t-butyl ester derivative with a solution of 1 ml of anisole in 5 ml of trifluoroacetic acid for two hours at 0° followed by concentration in vacuo. Crystallization occurred upon trituration with ether.

Analysis of salt: $C_{20}H_{20}N_6O_6S_3 \cdot CF_3COOH \cdot \frac{1}{2}(CH_3CH_2)_2O$ (669.187)

|   | Theory | Found |
|---|--------|-------|
| C | 41.28  | 41.68 |
| H | 3.54   | 3.72  |
| N | 12.56  | 13.09 |

The zwitterionic product is obtained as described in Example 6.

EXAMPLE 9

D-N-t-Butoxycarbonyl-p-t-butoxycarbonylethylthiophenylglycine

The title compound was obtained from reaction of p-amino-D-N-acetylphenylglycine, 3-bromopropionic acid t-butyl ester and diisopropylamine by the same procedure as described in Example 1.

D-p-carboxyethylthiophenylglycine is prepared as its salt by treating the title compound with trifluoroacetic acid as described in Example 1.

EXAMPLE 10

7-[D-α-Amino-α-(4'-carboxyethylthiophenyl)acetamido]-3-(5-methyl-1,3,4-thiadiazol-2-ylthiomethyl)-3-cephem -4-carboxylic acid (Compound No. 61726)

The title compound was obtained from reaction of 0.135 g (0.33 mmol) of D-N-t-butoxycarbonyl-p-t-butoxy- carbonylethylthiophenylglycine, 0.110 g (0.28 mmol) of 7-amino-3-(5-methyl-1,3,4-thiadiazol-2-ylthiomethyl)-3-cephem -4-carboxylic acid t-butyl ester, and 0.060 g (0.28 mmol) of dicyclohexylcarbodiimide by the same procedure as described in Example 6. Deblocking was accomplished by stirring the crude product with 0.5 ml of anisole and 5 ml of trifluoroacetic acid at 0° for one hour, then at 15° for 0.5 hour. The acid (0.105 g; 65%) was precipitated as its salt by trituration of the residue with ether.

| Analysis of switterion: $C_{22}H_{23}N_5O_6S_4 \cdot 1\ H_2O$ (599.746) | | |
|---|---|---|
| | Theory | Found |
| C | 44.06 | 43.72 |
| H | 4.20 | 3.89 |
| N | 11.67 | 11.45 |

EXAMPLE 11

D-N-t-butoxycarbonyl-p-carbamylmethylthiophenylglycine

A mixture of 1.0 g (3.7 mmol)of D-N-t-butoxycarbonyl-p-mercaptophenylglycine and 0.4 g (4.3 mmol) of a α-chloro-acetamide in 10 ml of ethanol was stirred under nitrogen with 1.0 ml of triethylamine for 4 hours. The reaction mixture was then diluted with water, acidified with dilute HCl and extracted with ethyl acetate. The organic phase was shaken with 5% sodium carbonate and the mixture was acidified then extracted with ethyl acetate. The extracts were washed with saturated sodium chloride solution, dried ($Na_2SO_4$), and concentrated to give a residue which was crystallized from ethanol (0.830 g; 66%).

D-p-carbamylmethylthiophenylglycine is obtained as its salt from treatment of the title compound with trifluoroacetic acid as described in Example 1.

EXAMPLE 12

7-[D-α-Amino-α-(4'-carbamylmethylthiophenyl-)acetamido]-3-(5-methyl-1,3,4-thiadiazol-2-ylthiomethyl)-3-cephem -4-carboxylic acid (Compound No. 86526)

The title compound was obtained from 0.175 g (0.52 mmol) of D-N-t-butoxycarbonyl-p-carbamylmethylthiophenylglycine, 0.200 g (C.50 mmol) of 7-amino-3-(5-methyl-1,3,4-thiadiazol-2-ylthiomethyl)-3-cephem-4-carboxylic acid t-butyl ester, and 0.120 g (0.58 mmol) of dicyclohexylcarbodiimide by the same procedure as described in Example 6. Before deblocking, the crude intermediate was purified by chromatography on silica gel with chloroform-ethyl acetate.

| Analysis of salt: $C_{21}H_{22}N_6O_5S_4 \cdot CF_3CO_2H$ | | |
|---|---|---|
| | Theory | Found |
| C | 40.58 | 41.25 |
| H | 3.41 | 3.72 |
| N | 12.35 | 12.85 |

The zwitterionic product is obtained as in Example 6.

EXAMPLE 13

D-N-t-Butoxycarbonyl-p-t-butoxycarbonylmethoxyphenylglycine

A solution of 25 g (0.129 mol) of diphenyldiazomethane in 210 ml of dry benzene was added dropwise to a stirred solution of 26.7 g (0.100 mol) of D-N-t-butoxycarbonyl-p-hydroxyphenylglycine in 200 ml of dry benzene and 30 ml of dry THF. After stirring at 25° for 4.5 hours, the reaction mixture was concentrated and the residue was dissolved in ether. The ethereal solution was washed with 5% sodium bicarbonate and with water, dried and concentrated in vacuo to yield a residue which was dissolved in a small volume of chloroform and precipitated by addition of pet. ether to give 34.8 g (80%) of D-N-t-butoxycarbonyl-p-hydroxyphenylglycine benzhydryl ester.

The benzhydryl ester (4.33 g; 0.01 mol) was stirred at 25° for 1.5 hours with 4 ml of α-bromoacetic acid t-butyl ester in 40 ml of dry dimethylformamide. The reaction mixture was diluted with water and extracted with ether. Concentration gave an oily residue which was heated (90°) in vacuo, then dissolved in 150 ml of ethanol and hydrogenolyzed over 2g of 10% palladium on carbon to give the title compound (3.2 g; 84%).

D-p-carboxymethoxyphenylglycine is obtained as its salt from treatment of the title compound with trifluoroacetic acid as described in Example 1.

EXAMPLE 14

7-[D-α-Amino-α-(4'carboxymethoxyphenyl-)acetamido]-3-(5-methyl-1,3,4-thiadiazol-2-ylthiomethyl)-3-cephem-4-carboxylic acid (Compound No. 59216)

The title compound was obtained from 0.87 g (2.28 mmol) of D-N-t-butoxycarbonyl-p-t-butoxycarbonylmethoxyphenylglycine, 0.92 g (2.3 mmol) of 7-amino-3-(5-methyl-1,3,4-thiadiazol-2-ylthiomethyl)-3-cephem-4-carboxylic acid t-butyl ester and 0.475 g (2.3 mmol) of dicyclohexylcarbodiimide by the same procedure as described in Example 6. The intermediate was purified by chromatography on silica gel with chloroform before deblocking.

| Analysis of zwitterion: $C_{21}H_{21}N_5O_7S_3 \cdot 2H_2O$ $0.2(C_2H_5)_2O$ (602.494) | | |
|---|---|---|
| | Theory | Found |
| C | 43.46 | 43.93 |
| H | 4.52 | 4.23 |
| N | 11.63 | 11.06 |

EXAMPLE 15

7-[DL-α-amino-α-(4'-carboxymethoxyphenyl-)acetamido]-3-desacetoxycephalosporanic acid (Compound No. 08016)

The title compound was obtained from 0.50 g (1.31 mmol) of DL-N-t-butoxycarbonyl-p-t-butoxycarbonvimethoxyphenylglycine, 0.372 g (1.38 mmol) of 7-amino-3-desacetoxycephalosporanic acid t-butyl ester and 0.27 g (1.31 mmol) of dicyclohexylcarbodiimide by the same procedure as described in Example 6.

| Analysis of zwitterion: $C_{18}H_{19}N_3O_7S \cdot 1\frac{1}{2}H_2O$ (448.464) | | |
|---|---|---|
| | Theory | Found |
| C | 48.21 | 48.45 |
| H | 4.94 | 4.92 |
| N | 9.37 | 9.12 |

EXAMPLE 16

7-[D-α-(Amino-α-(4'-carboxymethoxyphenyl-)acetamido]-cephalosporanic acid (Compound No. 60326)

The title compound was obtained from 0.656 g (0.002 mol) of 7ACA t-butyl ester, 0.762 g (0.002 mol) of D-N-t-butoxycarbonyl-p-t-butoxycarbonylmethoxyphenylglycine, and 0.412 g (0.002 mol) of dicyclohexylcarbodiimide by the same procedure as described in Example 6.

Analysis of salt: $C_{20}H_{21}N_3O_9S \cdot 0.4\ CF_3COOH \cdot 1.25\ H_2O$ (547.610)

|   | Theory | Found |
|---|---|---|
| C | 45.62 | 45.77 |
| H | 4.40  | 4.22  |
| N | 7.67  | 7.42  |
| F | 4.16  | 4.22  |

The zwitterionic product is obtained as described in Example 6.

EXAMPLE 17

7-[D-α-Amino-α-(4'-carboxymethoxyphenyl)acetamido]-3-(1,2,3-triazol-4-ylthiomethyl-3-cephem-4-carboxylic acid (Compound No. 03326)

The title compound was obtained from 0.500 g (1.6 mmol) of 7-amino-3-(1,2,3-triazol-4-ylthiomethyl)-3-cephem-4-carboxylic acid and 0.780 g (1.6 mmol) of the activated ester of D-N-t-butoxycarbonyl-p-t-butoxycarbonylmethoxyphenylglycine by the same procedure as described in Example 8.

Analysis of zwitterion: $C_{20}H_{20}N_6O_7S_2 \cdot 1.75\ H_2O$ (552.088)

|   | Theory | Found |
|---|---|---|
| C | 43.51 | 44.04 |
| H | 4.29  | 4.19  |
| N | 15.22 | 13.57 |

EXAMPLE 18

7-[D-α-Amino-α-(4'-carboxymethoxyphenyl)acetamido]-3-(1-methyl-1,2,3,4-tetrazol-5-ylthiomethyl)-3-cephem-4-carboxylic acid (Compound No. 42526)

The title compound was obtained from 0.84 g (2.55 mmol) of 7-amino-3-(1-methyl-1,2,3,4-tetrazol-5-ylthiomethyl)-3-cephem-4-carboxylic acid and 1.22 g (2.55 mmol) of the activated ester of D-N-t-butoxycarbonyl-p-t-butoxycarbonylmethoxyphenylglycine by the same procedure as described in Example 8.

Analysis of zwitterion: $C_{20}H_{21}N_7O_7S_2 \cdot 1\ H_2O$ (533.592)

|   | Theory | Found |
|---|---|---|
| C | 43.39 | 43.28 |
| H | 4.19  | 4.10  |
| N | 17.71 | 15.77 |

EXAMPLE 19

D-N-t-Butoxycarbonyl-p-carbamylmethoxyphenylglycine

A mixture of 0.433 g (1.0 mmol) of D-N-t-butoxycarbonyl-p-hydroxyphenylglycine benzhydryl ester, 0.555 g (3.0 mmol) of α-iodoacetamide and 0.414 g (3.0 mmol) of potassium carbonate in 10 ml of dry dimethylformamide was stirred at 25° for 12 hours. The reaction mixture was then diluted with water and extracted twice with ethyl acetate. The extracts were washed (H₂0), dried (NaSO₄) and concentrated in vacuo to give 0.4 g (81.5%) of a residue which crystallized when dissolved in ether and triturated with pet. ether.

The product from above (3.9 g; 7.35 mmol) was dissolved in 50 ml of glacial acetic acid and hydrogenolyzed over 1.0 g of 10% palladium on carbon to give 1.7 g (66%) of the title compound.

D-p-carbamymethoxyphenylglycine is obtained as its salt from treatment of the title compound with trifluoroacetic acid as described in Example 1.

EXAMPLE 20

7-[D-α-(4'-carbamylmethoxyphenyl)acetamido]-3-desacetoxycephalosporanic acid. (Compound No. 00036)

The title compound was obtained from 0.81 g (2.5 mmol) of D-N-t-butoxycarbonyl-p-carbamylmethoxyphenylglycine, 0.675 g (2.5 mmol) of 7-amino-3-desacetoxycephalosporanic acid t-butyl ester and 0.515 g (2.5 mmol) of dicyclohexylcarbodiimide by the same procedure as described in Example 6. Before deblocking, the crude intermediate was purified by chromatography on silica gel.

Analysis of Salt: $C_{18}H_{20}N_4O_6S \cdot \tfrac{1}{2}CF_3COOH \cdot \tfrac{3}{2} H_2O$ (490.983)

|   | Theory | Found |
|---|---|---|
| C | 46.48 | 46.51 |
| H | 4.52  | 4.59  |
| N | 11.41 | 11.29 |

The zwitterionic product is obtained as described in Example 6.

EXAMPLE 21

7-[D-α-Amino-α-(4'-carbamylmethoxyphenyl)acetamido]-3-(5-methyl-1,3,4-thiadiazol-2-ylthiomethyl)-3-cephem-4-carboxylic acid (Compound No. 71816)

The title compound was obtained from 0.648 g (2.0 mmol) of D-N-t-butoxycarbonyl-p-carbamylmethoxyphenylglycine, 0.800 g (2.0 mmol) of 7-amino-3-(5-methyl-1,3,4-thiadiazol-2-ylthiomethyl)-3-cephem-4-carboxylic acid t-butyl ester and 0.412 g (2.0 mmol) of dicyclohexylcarbodiimide by the same procedure as described in Example 6.

Analysis of zwitterion: $C_{21}H_{22}N_6O_6S_3 \cdot 1\ H_2O \cdot \tfrac{1}{4}(C_2H_5)_2O$ (587.200)

|   | Theory | Found |
|---|---|---|
| C | 45.00 | 45.13 |
| H | 4.55  | 4.54  |
| N | 14.31 | 13.90 |

EXAMPLE 22

7-[D-α-Amino-α-(4'-carbamylmethoxyphenyl)acetamide]-3-(1,2,3-triazol-4-ylthiomethyl)-3-cephem-4-carboxylic acid (Compound No. 91726)

The title compound was obtained from 0.855 g (2.73 mmol) of 7-amino-3-(1,2,3-triazol-4-ylthiomethyl)-3-cephem-4-carboxylic acid and 1.15 g (2.73 mmol) of the activated ester of D-N-t-butoxycarbonyl-p-carbamylmethoxyphenylglycine by the same procedure as described in Example 8.

| Analysis of salt: $C_{20}H_{21}N_7O_6S_2 \cdot CF_3COOH \cdot 1 H_2O \cdot \frac{1}{2}$ $(C_2H_5)_2O$ (688.684) | | |
|---|---|---|
| | Theory | Found |
| C | 41.86 | 42.20 |
| H | 4.24 | 3.97 |
| N | 14.24 | 13.71 |
| F | 8.28 | 8.06 |

The zwitterionic product is obtained as described in Example 6.

EXAMPLE 23

7-[D-α-Amino-α-(4'-carbamylmethoxyphenyl-)acetamido]-3-(1-methyl-1,2,3,4-tetrazol-5-ylthiomethyl)-3-cephem-4-carboxylic acid (Compound No. 32626)

The title compound was obtained from 0.985 g (3.0 mmol) of 7-amino-3-(1-methyl-1,2,3,4-tetrazol-5-ylthiomethyl)-3-cephem-4-carboxylic acid and 1.30 g (3.1 mmol) of the activated ester of D-N-t-butoxycarbonyl-p-carbamylmethoxyphenylglycine by the same procedure as described in Example 8.

| Analysis of zwitterion: $C_{20}H_{22}N_8O_6S_2 \cdot \frac{1}{2} H_2O$ (543.600) | | |
|---|---|---|
| | Theory | Found |
| C | 44.19 | 44.26 |
| H | 4.26 | 4.33 |
| N | 20.62 | 17.44 |

EXAMPLE 24

D-N-t-Butoxycarbonyl-p-carbomethoxymethoxyphenylglycine

The title compound was obtained from 4.33 g (0.01 mol) of D-N-t-butoxycarbonyl-p-hydroxyphenylglycine benzhydryl ester, 4 ml of α-bromoacetic acid methyl ester and 3 g (0.022 mol) of potassium carbonate by the same procedure was described in Example 13.

D-p-carbomethoxymethoxyphenylglycine is obtained as its salt by treatment of the title compound with trifluoroacetic acid as described in Example 1.

EXAMPLE 25

7-[D-α-Amino-α-(4'-carbomethoxymethoxyphenyl-)acetamido]-3-desacetoxycephalosporanic acid (Compound No. 07826)

The title compound was obtained from 0.675 g (2.5 mmol) of 7-ADCA t-butyl ester, 0.85 g (2.5 mmol) of D-N-t-butoxycarbonyl-p-carbomethoxymethoxyphenylglycine and 0.515g (2.5 mmol) of dicyclohexylcarbodiimide by the same procedure as described in Example 6. The initial reaction mixture was stirred at 25° for 5 hours.

| Analysis of salt: $C_{19}H_{21}N_3O_7S \cdot CF_3COOH$ (549.497) | | |
|---|---|---|
| | Theory | Found |
| C | 45.90 | 45.70 |
| H | 4.04 | 4.11 |
| N | 7.65 | 7.61 |

EXAMPLE 26

7-[D-α-Amino-α-(4'-carbomethoxymethoxyphenyl-)acetamidol-3-(5-methyl-1,3,4-thiadiazol-2-ylthiomethyl)-3-cephem-4-carboxylic acid (Compound No. 96826)

The title compound was obtained from 1.00 g (2.5 mmol) of 7-amino-3-(5-methyl-1,3,4-thiadiazol-2-ylthiomethyl)-3-cephem-4-carboxylic acid t-butyl ester, 0.85 g (2.5 mmol) of D-N-t-butoxycarbonyl-p-carbomethoxymethoxyphenylglycine and 0.515 g (2.5 mmol) of dicyclohexylcarbodiimide by the same procedure as described in Example 6. The initial reaction mixture was stirred, at 25° for 2 hours.

| Analysis of zwitterion: $C_{22}H_{23}N_5O_7S_3$ (565.664) | | |
|---|---|---|
| | Theory | Found |
| C | 46.72 | 46.49 |
| H | 4.10 | 4.16 |
| N | 12.38 | 12.11 |

EXAMPLE 27

7-[D-α-Amino-α-(4'-carbomethoxymethoxyphenyl-)acetamido]-3-(1,2,3-triazol-4-ylthiomethyl)-3-cephem-4-carboxylic acid (Compound No. 19736)

The title compound was obtained from 1.55 g (3.56 mmol) of the activated ester of D-N-t-butoxycarbonyl-p-carbomethoxymethoxyphenylglycine, 1.11 g (3.56 mmol) of 7-amino-3-(1,2,3-triazol-4-ylthiomethyl)-3-cephem-4-carboxylic acid and 0.72 g (7.12 mmol) of triethylamine by the same procedure as described in Example 8.

| Analysis of salt: $C_{21}H_{22}N_6O_7S_2 \cdot \frac{1}{2} CF_3COOH \cdot \frac{1}{2} H_2O$ (600.583) | | |
|---|---|---|
| | Theory | Found |
| C | 44.00 | 44.09 |
| H | 3.94 | 4.06 |
| N | 13.99 | 13.59 |

EXAMPLE 28

7-[D-α-Amino-α-(4'-carbomethoxymethoxyphenyl-)acetamidol-3-(1methyl-1,2,3-tetrazol-5-ylthiomethyl)-3-cephem-4-carboxylic acid (Compound No. 26436)

The title compound was obtained from 1.00 g (2.6 mmol) of 7-amino-3-(1-methyl-1,2,3,4-tetrazol-5-ylthiomethyl)-3-cephem-4-carboxylic acid t-butyl ester, 0.883 g (2.6 mmol) of D-N-t-butoxycarbonyl-p-carbomethoxymethoxyphenylglycine and 0.536 g (2.6 mmol) of dicyclohexylcarbodiimide by a procedure simmilar to that described in Example 6. The initial reaction mixture was stirred for 12 hours at 25° before work-up. Deblocking was accomplished by stirring a mixture of the crude adduct and 2 ml of benzenethiol in 10 ml of trifluoroacetic acid at 25° for 1 hour. Concentration of the reaction mixture gave a residue which crystallized upon addition of ether and was recrystallized from ethanol-ether (0.500 g).

| Analysis of zwitterion: $C_{21}H_{23}N_7O_7S_2 \cdot 1 H_2O$ (567.619) | | |
|---|---|---|
| | Theory | Found |
| C | 44.44 | 44.33 |
| H | 4.44 | 4.35 |

-continued

Analysis of zwitterion: $C_{21}H_{23}N_7O_7S_2 \cdot 1\ H_2O$
(567.619)

|   | Theory | Found |
|---|--------|-------|
| N | 17.27  | 16.60 |

EXAMPLE 29

D-N-t-Butoxycarbonyl-p-t-butoxycarbonylmethylaminophenylglycine

A mixture of 2.5 g (7.7 mmol) of D-N-t-butoxycarbonyl-p-aminophenylglycine, 1.8 g (9.2 mmol) of α-bromoacetic acid t-butyl ester and 2.5 g (19.3 mmol) of diisopropyl ethylamine in 15 ml of ethanol was stirred at 25° for 48 hours. The solvent was removed in vacuo, the residue was diluted with ethyl acetate and sodium bicarbonate and the pH was adjusted to 2.5. The layers were separated and the aqueous phase was again extracted with ethyl acetate. The combined extracts were washed with saturated sodium chloride solution, dried (MgSO$_4$) and concentrated to give 1.1 g (32%) of the title compound.

D-p-carboxymethylaminophenylglycine is obtained as its salt by treating the title compound with trifluoroacetic acid as described in Example 1.

EXAMPLE 30

7-[D-α-Amino-α-(4'-carboxymethylaminophenyl-)acetamido]-3-desacetoxycephalosporanic acid (Compound No. 51436)

The title compound was obtained from 0.240 g (1.0 mmol) of 7-ADCA t-butyl ester, 0.380 g (1.0 mmol) of D-N-t-butoxycarbonyl-p-t-butoxycarbonylmethylaminophenylglycine and 0.210 g (1.0 mmol) of dicyclohexylcarbodiimide in 9:1 ethyl acetate-methylene chloride by the same procedure as described in Example 6. Before deblocking, the intermediate was purified by chromatography on silica gel with methylene chloride-ethyl acetate-acetic acid (4:1:.01). Deblocking was accomplished by the procedure described in Example 28.

Analysis of zwitterion: $C_{19}H_{20}N_4O_6S \cdot 1.5\ H_2O$
(447.480)

|   | Theory | Found |
|---|--------|-------|
| C | 48.32  | 48.53 |
| H | 5.18   | 4.88  |
| N | 12.52  | 12.34 |

EXAMPLE 31

7-[D-α-Amino-α-(4'-carboxymethylaminophenyl-)acetamido]-3-(5-methyl-1,3,4-thiadiazol 2-ylthiomethyl)-3-cephem-4-carboxylic acid (Compound No. 48536)

The title compound was obtained from 0.66 g (1.77 mmol) of D-N-t-butoxycarbonyl-p-t-butoxycarbonylmethylaminophenylglycine, 0.652 g (1.77 mmol) of 7-amino-3-(5-methyl-1,3,4,-thiadiazol-2-ylthiomethyl)-3-cephem-4-carboxylic acid t-butyl ester and 0.376 g (1.77 mmol) of dicyclohexylcarbodiimide in 18 ml of ethyl acetate and 2 ml of methylene chloride by the same procedure as described in Example 6. The initial reaction mixture was stirred at 0° for 1 hour, then at 25° for 2 hours. Before deblocking, the intermediate was purified by chromatography on silica gel with ethyl acetate-benzene. Deblocking was accomplished by the procedure described in Example 28.

Analysis of salt: $C_{21}H_{22}N_6O_6S_3 \cdot CF_3COOH \cdot 1(C_2H_5)_2O$
(738.807)

|   | Theory | Found |
|---|--------|-------|
| C | 43.89  | 43.61 |
| H | 4.50   | 4.49  |
| N | 11.38  | 11.61 |

EXAMPLE 32

D-N-t-Butoxycarbonyl-p-carbomethyoxymethylaminophenylglycine

Substitution of an equivalent amount of α-bromoacetic acid methyl ester in the procedure of Example 29 for α-bromoacetic acid t-butyl ester, followed by chromatography of the crude product on silica gel with 4:1:0.01 methylene chloride-ethyl acetate-acetic acid gave the title compound.

D-p-carbomethyoxymethylaminophenylglycine is obtained as its salt by treatment of the title compound with trifluoroacetic acid as described in Example 1.

EXAMPLE 33

7-[D-α-Amino-α-(4'-carbomethyoxymethylaminophenyl)-acetamido]-3-(5-methyl-1,3,4-thiadiazol-2-ylthiomethyl)-3-cephem-4-carboxylic acid (Compound No. 96146)

The title compound was obtained from 0.338 g (1mmol) of D-N-t-butoxycarbonyl-p-carbomethyloxymethylaminophenylglycine, 0.368 g (1mmol) of 7-amino-3-(5-methyl-1,3,4-thiadiazol-2-ylthiomethyl)-3-cephem-4-carboxylic acid t-butyl ester and 0.212 g (1mmol) of dicyclohexylcarbodiimide in 20 ml of methylene chloride by the same procedure as described in Example 6. The initial reaction mixture was stirred at 0° for 30 minutes then at 25° for 2 hours. Before deblocking, the intermediate was chromatographed on silica gel with ethyl acetate-benzene. Deblocking was accomplished by stirring a mixture of 0.2 g of 7-[D-α-t-butoxycarbonylamino-α-(4'-carbomethoxymethylaminophenyl) acetamido]-3-(5-methyl-1,3,4-thiadiazol-2-ylthiomethyl)-3-cephem-4-carboxylic acid t-butyl ester and 0.5 ml of benzenethiol in 4.5 ml of trifluoroacetic acid at 0° for 30 minutes, then at 25° for 1.5 hours. The reaction mixture was concentrated and the residue triturated with ether to give the title compound (0.2 g) as its salt, which was recrystallized from methanol-ether.

Analysis of salt: $C_{22}H_{24}N_6O_6S_3 \cdot 0.7\ CF_3CO_2H$
(644.480)

|   | Theory | Found |
|---|--------|-------|
| C | 43.61  | 43.42 |
| H | 3.86   | 4.23  |
| N | 13.04  | 13.34 |

EXAMPLE 34

When an equivalent amount of the t-butyl ester of a 7-amino-3-heterocyclicthiomethyl-3-cephem-4-carboxylic acid listed below is substituted in the procedure of Example 6 for 7-amino-3-(5-methyl-1,3,4-thiadiazol-2-ylthiomethyl)-3-cephem-4-carboxylic acid t-butyl ester, the appropriate 7-[α-amino-α-(4'-carboxymethylthiophenyl)acetamido]-3-heterocyclicthiomethyl-3-cephem-4-carboxylic acid is obtained:

7-amino-3-(1,3,4-thiadiazol-2-ylthiomethyl-3-cephem-4-carboxylic acid.
7-amino-3-(5-ethyl-1,3,4-thiadiazol-2-ylthiomethyl-3-cephem-4-carboxylic acid.
7-amino-3-(5-trifluoromethyl-1,3,4-thiadiazol-2-ylthiomethyl-3-cephem-4-carboxylic acid.
7-amino-3-(5-n-butyl-1,3,4-thiadiazol-2-ylthiomethyl-3-cephem-4-carboxylic acid.
7-amino-3-(1,3,4-thiadiazol-5-ylthiomethyl-3-cephem-4-carboxylic acid.
7-amino-3-(3-methyl-1,2,4-thiadiazol-5-ylthiomethyl-3-cephem-4-carboxylic acid.
7-amino-3-(3-ethyl-1,2,4-thiadiazol-5-ylthiomethyl-3-cephem-4-carboxylic acid.
7-amino-3-(thiazol-5-ylthiomethyl-3-cephem-4-carboxylic acid.
7-amino-3-(2-methylthiazol-5-ylthiomethyl-3-cephem-4-carboxylic acid.
7-amino-3-(4-methylthiazol-5-ylthiomethyl-3-cephem-4-carboxylic acid.
7-amino-3-(2,4-dimethylthiazol-5-ylthiomethyl-3-cephem-4-carboxylic acid.
7-amino-3-(1,3,4-oxadiazol-2-ylthiomethyl-3-cephem-4-carboxylic acid.
7-amino-3-(5-methyl-1,3,4-oxadiazol-2-ylthiomethyl-3-cephem-4-carboxylic acid.
7-amino-3-(2-methyloxazol-5-ylthiomethyl)-3-cephem-4-carboxylic acid.
7-amino-3-(oxazol-5-ylthiomethyl)-3-cephem-4-carboxylic acid.
7-amino-3-(4-methyloxazol-5-ylthiomethyl)-3-cephem-4-carboxylic acid.
7-amino-3-(2,4-dimethyloxazol-5-ylthiomethyl)-3-cephem-4-carboxylic acid.
7-amino-3-(1,2,3,4-tetrazol-5-ylthiomethyl)-3-cephem-4-carboxylic acid.
7-amino-3-(1-ethyl-1,2,3,4-tetrazol-5-ylthiomethyl)-3-cephem-4-carboxylic acid.
7-amino-3-(1-methoxymethyl-1,2,3,4-tetrazol-5-ylthiomethyl)-3-cephem-4-carboxylic acid.
7-amino-3-(1,2,4-triazol-3-ylthiomethyl)-3-cephem-4-carboxylic acid.
7-amino-3-(4-methyl-1,2,4-triazol-3-ylthiomethyl)-3-cephem-4-carboxylic acid.
7-amino-3-(5-methyl-1,2,4-triazol-3-ylthiomethyl)-3-cephem-4-carboxylic acid.
7-amino-3-(1-methyl-1,2,4-triazol-5-ylthiomethyl)-3-cephem-4-carboxylic acid.
7-amino-3-(1-methyl-1,2,4-triazol-3-ylthiomethyl)-3-cephem-4-carboxylic acid.
7-amino-3-(1,5-dimethyl-1,2,4-triazol-3-ylthiomethyl)-3-cephem-4-carboxylic acid.
7-amino-3-(1,3-dimethyl-1,2,4-triazol-3-ylthiomethyl)-3-cephem-4-carboxylic acid.
7-amino-3-(4,5-dimethyl-1,2,4-triazol-3-ylthiomethyl)-3-cephem-4-carboxylic acid.
7-amino-3-(5-methoxymethyl-1,2,4-triazol-3-ylthiomethyl)-3-cephem-4-carboxylic acid.
7-amino-3-(4-methyl-5-trifluoromethyl-1,2,4triazol-3-ylthiomethyl)-3-cephem-4-carboxylic acid.
7-amino-3-(4-allyl-1,2,4triazol-3-ylthiomethyl)-3-cephem-4-carboxylic acid.
7-amino-3-(5-hydroxy-4-methyl-1,2,4triazol-3-ylthiomethyl)-3-cephem-4-carboxylic acid.
7-amino-3-(4-ethyl-5-hydroxy-1,2,4-triazol-3-ylthiomethyl)-3-cephem-4-carboxylic acid.
7-amino-3-(1-methyl-1,2,3-triazol-4-ylthiomethyl)-3-cephem-4-carboxylic acid.
7-amino-3-(5-methyl-1,2,3-triazol-4-ylthiomethyl)-3-cephem-4-carboxylic acid.
7-amino-3-(3,5-dimethyl-1,2,3-triazol-4-ylthiomethyl)-3-cephem-4-carboxylic acid.
7-amino-3-(5-methylthio-1,2,3-triazol-4-ylthiomethyl)-3-cephem-4-carboxylic acid.
7-amino-3-(5-methoxymethyl-1,2,3-triazol-4-ylthiomethyl)-3-cephem-4-carboxylic acid.
7-amino-3-(4-pyridylthiomethyl)-3-cephem-4-carboxylic acid.
7-amino-3-(3-pyridylthiomethyl)-3-cephem-4-carboxylic acid.
7-amino-3-(4-pyrimidylthiomethyl)-3-cephem-4-carboxylic acid.
7-amino-3-(2-pyrazinylthiomethyl)-3-cephem-4-carboxylic acid.

EXAMPLE 35

When an equivalent amount of the t-butyl ester of a 7-amino-3-heterocyclic thiomethyl-3-cephem-4-carboxylic acid listed in Example 34 is substituted in the procedure of Example 10 for 7-amino-3-(5-methyl-1,3,4-thiadiazol-2-ylthiomethyl)-3-cephem-4-carboxylic acid t-butyl ester, the appropriate 7-[α-amino-α-(4'-carboxyethylthiophenyl)acetamido]-3-heterocyclic thiomethyl-3-cephem-4-carboxylic acid is obtained.

EXAMPLE 36

When an equivalent amount of the t-butyl ester of a 7-amino-3-heterocyclic thiomethyl-3-cephem-4-carboxylic acid listed in Example 34 is substituted in the procedure of Example 12 for 7-amino-3-(5-methyl-1,3,4-thiadiazol-2-ylthiomethyl)-3-cephem-4-carboxylic acid t-butyl ester, the appropriate 7-[α-amino-α-(4'-carbamylmethylthiophenyl)acetamido]-3-heterocyclic thiomethyl-3-cephem-4-carboxylic acid is obtained.

EXAMPLE 37

When an equivalent amount of the t-butyl ester of a 7-amino-3-heterocyclic thiomethyl-3-cephem-4-carboxylic acid listed in Example 34 is substituted in the procedure of Example 14 for 7-amino-3-(5-methyl-1,3,4-thiadiazol-2-ylthiomethyl)-3-cephem-4-carboxylic acid t-butyl ester, the appropriate 7-[α-amino-α-(4'-carboxymethoxyphenyl)acetamido]-3-heterocyclicthiomethyl-3-cephem-4-carboxylic acid is obtained.

EXAMPLE 38

When an equivalent amount of the t-butyl ester of a 7-amino-3-heterocyclic thiomethyl-3-cephem-4-carboxylic acid listed in Example 34 is substituted in the procedure of Example 21 for 7-amino-3-(5-methyl-1,3,4-thiadiazol-2-ylthiomethyl)-3-cephem-4-carboxylic acid t-butyl ester, the appropriate 7-[α-amino-α-(4'-carbamylmethoxyphenyl)acetamido]-3-heterocyclic thiomethyl-3-cephem-4-carboxylic acid is obtained.

EXAMPLE 39

When an equivalent amount of the t-butyl ester of a 7-amino-3-heterocyclic thiomethyl-3-cephem-4-carboxylic acid listed in Example 34 is substituted in the procedure of Example 26 for 7-amino-3-(5-methyl-1,3,4-thiadiazol-2-ylthiomethyl)-3-cephem-4-carboxylic acid t-butyl ester, the appropriate 7-[α-amino-α(4'-carbomethoxymethoxyphenyl)acetamido]-3-heterocyclic thiomethyl-3-cephem-4-carboxylic acid is obtained.

EXAMPLE 40

When an equivalent amount of the t-butyl ester of a 7-amino-3-heterocyclic thiomethyl-3-cephem-4-carboxylic acid listed in Example 34 is substituted in the procedure of Example 31 for 7-amino-3-(5-methyl-1,3,4-thiadiazol-2-ylthiomethyl)-3-cephem-4-carboxylic acid t-butyl ester, the appropriate 7-[α-amino-α-(4'-carboxymethylaminophenyl)acetamido]-3-heterocyclic thiomethyl-3-cephem-4-carboxylic acid is obtained.

EXAMPLE 41

When an equivalent amount of the t-butyl ester of a 7-amino-3-heterocyclic thiomethyl-3-cephem-4-carboxylic acid listed in Example 34 is substituted in the procedure of Example 33 for 7-amino-3-(5-methyl-1,3,4-thiadiazol-2-ylthiomethyl)-3-cephem-4-carboxylic acid t-butyl ester, the appropriate 7-[α-amino-α-(4'-carbomethoxymethylaminophenyl)acetamido]-3-heterocyclic thiomethyl-3-cephem-4-carboxylic acid is obtained.

EXAMPLE 42

7-[D-α-Amino-α-(3'-carboxymethylthiophenyl)acetamido]-3-(1-methyl-1,2,3,4-tetrazol-5-ylthiomethyl)-3-cephem-4-carboxylic acid The title compound is obtained from reaction of 0.5 g (1.28 mmol) of D-N-t-butoxycarbonyl-m-t-butoxycarbonylmethylthiophenylglycine, 0.5 g (1.3 mmol) of 7-amino-3-(1-methyl-1,2,3,4-tetrazol-5-ylthiomethyl-3-cephem-4-carboxylic acid t-butyl ester and 0.265 g (1.3 mmol) of dicyclohexylcarbodiimide by the same procedure as described in Example 6.

EXAMPLE 43

When an equivalent amount of the t-butyl ester of 7-amino-3-desacetoxycephalosporanic acid, 7-amino-3-(5-methyl-1,3,4-thiadiazol-2-ylthiomethyl)-3-cephem-4-carboxylic acid, 7-amino-3-(1,2,3-triazol-4-ylthiomethyl)-3-cephem-4-carboxylic acid, or a 7-amino-3-heterocyclic thiomethyl-3-cephem-4 carboxylic acid listed in Example 34 is substituted in the procedure of Example 42 for 7-amino-3-(1-methyl-1,2,3,4-tetrazol-5-ylthiomethyl)-3-cephem-4-carboxylic acid t-butyl ester, the appropriate 7-[α-amino-α-(3'carboxymethylthiophenyl)acetamido]-3-heterocyclic thiomethyl-3-cephem-4-carboxylic acid is obtained.

EXAMPLE 44

7-[D-α-Amino-α-(3'-carboxymethylaminophenyl)acetamido]-3-(5-methyl-1,3,4-thiadiazol-2-ylthiomethyl)-3-cephem-4-carboxylic acid.

The title compound is obtained from reaction of 0.66 g (1.77 mmol) of D-N-t-butoxycarbonyl-m-t-butoxycarbonylmethylaminophenylglycine, 0.652 g (1.77 mmol) of 7-amino-3-(5-methyl-1,3,4-thiadiazol-2-ylthiomethyl)-3-cephem-4-carboxylic acid t-butyl ester and 0.376 g (1.77 mmol) of dicyclohexylcarbodiimide by the same procedure as described in Example 31.

EXAMPLE 45

When an equivalent amount of the t-butyl ester of 7-amino-3-desacetoxycephalosporanic acid, 7-amino-3(1-methyl-1,2,3,4-tetrazol-5-ylthiomethyl)-3-cephem-4-carboxylic acid, 7-amino-3-(1,2,3-triazol-4-ylthiomethyl)-3-cephem-4-carboxylic acid or a 7-amino-3-heterocyclic thiomethyl-3-cephem-4-carboxylic acid listed in Example 34 is substituted in the procedure of Example 44 for 7-amino-3-(5-methyl-1,3,4-thiadiazol-2-ylthiomethyl)-3-cephem-4-carboxylic acid t-butyl ester, the appropriate 7-[α-amino-α-(3'-carboxymethylaminophenyl)acetamido]-3-heterocyclic thiomethyl-3-cephem-4-carboxylic acid is obtained.

EXAMPLE 46

7-[α-Amino-α-(3'-carbamylmethoxyphenyl)acetamido]-3-(5-methyl-1,3,4-thiadiazol-2-ylthiomethyl)-3-cephem-4-carboxylic acid.

The title compound is obtained from reaction of 0.648 g (2.0 mmol) of D-N-t-butoxycarbonyl-m-carbamylmethoxyphenylglycine, 0.800 g (2.0 mmol) of 7-amino-3-(5-methyl-1,3,4-thiadiazol-2-ylthiomethyl)-3-cephem-4-carboxylic acid t-butyl ester and 0.412 g (2.0 mmol) of dicyclohexylcarbodiimide by the same procedure as described in Example 6.

EXAMPLE 47

When an equivalent amount of the t-butyl ester of 7-amino-3-desacetoxycephalosporanic acid, 7-amino-3-(1-methyl-1,2,3,4-tetrazol-5-ylthiomethyl)-3-cephem-4-carboxylic acid, 7-amino-3-(1,2,3-triazol-4-ylthiomethyl)-3-cephem-4-carboxylic acid or a 7-amino-3-heterocyclicthiomethyl-3-cephem-4-carboxylic acid listed in Example 34 is substituted in the procedure of Example 46 for 7-amino-3-(5-methyl-1,3,4-thiadiazol-2-ylthiomethyl)-3-cephem-4-carboxylic acid t-butyl ester, the appropriate 7-[α-amino-α-(3'-carbamylmethoxyphenyl)acetamido]-3-heterocyclicthiomethyl-3-cephem-4-carboxylic acid is obtained.

EXAMPLE 48

7-[α-Amino-α-(2'-carboxymethylthiophenyl)acetamido]-3-(1-methyl-1,2,3,4-tetrazol-5-ylthiomethyl)-3-cephem-4-carboxylic acid The title compound is obtained from reaction of 0.5 g (1.28 mmol) of D-N-t-butoxycarbonyl-o-t-butoxycarbonylmethylthiophenylglycine, 0.5 g (1.3 mmol) of 7-amino-3-(1-methyl-1,2,3,4-tetrazol-5-ylthiomethyl)-3-cephem-4-carboxylic acid t-butyl ester and 0.265 g (1.3 mmol) of dicyclohexylcarbodiimide by the same procedure as described in Example 6.

EXAMPLE 49

When an equivalent amount of the t-butyl ester of 7-amino-3-desacetoxycephalosporanic acid, 7-amino-3-(5-methyl-1,3,4-thiadiazol-2-ylthiomethyl)-3-cephem-4-carboxylic acid, 7-amino-3-(1,2,3-triazol-4-ylthiomethyl)-3-cephem-4-carboxylic acid or a 7-amino-3-heterocyclothiomethyl-3-cephem-4-carboxylic acid listed in Example 34 is substituted in the procedure of Example 48 for 7-amino-3-(1-methyl-1,2,3,4-tetrazol-5-ylthiomethyl-3-cephem-4-carboxylic acid t-butyl ester, the appropriate 7-[α-amino-α-(2'-carboxymethylthiophenyl)acetamido]-3-heterocyclicthiomethyl-3-cephem-4-carboxylic acid is obtained.

EXAMPLE 50

7-[α-Amino-α-(2'-carboxymethylaminophenyl)acetamido]-3-(5-methyl-1,3,4-thiadiazol-2-ylthiomethyl)-3-cephem-4-carboxylic acid The title compound is obtained from reaction of 0.66 g (1.77 mmol) of D-N-t-butoxycarbonyl-o-t-butoxycarbonylmethylaminophenylglycine, 0.652 g (1.77 mmol) of 7-amino-3-(5-methyl-1,3,4-thiadiazol-2-ylthiomethyl-3-cephem-4-carboxylic acid t-butyl ester and 0.376 g (1.77 mmol) of dicyclohexylcarbodiimide by the same procedure as described in Example 31.

EXAMPLE 51

When an equivalent amount of the t-butyl ester of 7-amino-3-desacetoxycephalosporanic acid, 7-amino-3-(1-methyl-1,2,3,4-tetrazol-5-ylthiomethyl)-3-cephem-4-carboxylic acid, 7-amino-3-(1,2,3-triazol-4-ylthiomethyl)-3-cephem-4-carboxylic acid or a 7-amino-3-heterocyclicthiomethyl-3-cephem-4; -carboxylic acid listed in Example 34 is substituted in the procedure of Example 50 for 7-amino-3-(5-methyl-1,3,4-thiadiazol-2-ylthiomethyl)-3-cephem-4-carboxylic acid t-butyl ester, the appropriate 7-[α-amino-α-(2'-carboxymethylaminophenyl)acetamido]-3-heterocyclicthiomethyl-3-cephem-4-carboxylic acid is obtained.

EXAMPLE 52

7-[α-Amino-α-(2'-carbamylmethoxyphenyl)acetamido]-3-(5-methyl-1,3,4-thiadiazol-2-ylthiomethyl)-3-cephem-4-carboxylic acid The title compound is obtained from reaction of 0.648 g (2.0 mmol) of D-N-t-butoxycarbonyl-o-carbamylmethoxyphenylglycine, 0.800 g (2.0 mmol) of 7-amino-3-(5-methyl-1,3,4-thiadiazol-2-ylthiomethyl)-3-cephem-4-carboxylic acid t-butyl ester and 0.412 g (2.0 mmol) of dicyclohexylcarbodiimide by the same procedure as described in Example 6.

EXAMPLE 53

When an equivalent amount of the t-butyl ester of 7-amino-3-desacetoxycephalosporanic acid, 7-amino-3-(1-methyl-1,2,3,4-tetrazol-5-ylthiomethyl)-3-cephem-4-carboxylic acid, 7-amino-3-(1,2,3-triazol-4-ylthiomethyl)-3-cephem-4-carboxylic acid or a 7-amino-3-heterocyclicthiomethyl-3-cephem-4-carboxylic acid listed in Example 34 is substituted in the procedure of Example 52 for 7-amino-3-(5-methyl-1,3,4-thiadiazol-2-ylthiomethyl)-3-cephem-4-carboxyalic acid t-butyl ester, the appropriate 7-[amino-α-(2'-carbamylmethoxyphenyl)acetamido]-3-heterocyclicthiomethyl-3-cephem-4-carboxylic acid is obtained.

EXAMPLE 54

7-[α-amino-α-(4'-carboxymethylthiophenyl)acetamido]-3-(1-pyridiniummethyl)-3-cephem-4-carboxylic acid To a solution of 5.4 g (0.01 mol) of 7-[α-amino-α-(4'-carboxymethylthiophenyl)acetamido]cephalosporanic acid sodium salt in 25 ml of water is added 2.23 g (0.023 mol) of potassium thiocyanate and 2 ml (0.028 mol) of pyridine. The reaction mixture is heated at 65°–70° for 7 hours. After cooling, the mixture is diluted with 100 ml of water and the aqueous solution is chromatographed on a column of crosslinked polystyrene polymer (Amberlite XAD-2). The inorganic salts are eluted with water, then the product is eluted with 95% ethanol. Evaporation of the eluent gives the title compound.

EXAMPLE 55

7-]α-amino-α-(4'-carboxymethylthiophenyl)acetamidol-3-methylthiomethyl-3-cephem-4-carboxylic acid Acylation of 7-amino-3-methylthiomethyl-3-cephem-4-carboxylic acid (Belgian Pat. No. 743,754) with D-N-t-butoxycarbonyl-p-t-butoxycarbonylmethylthiophenylglycine according to the procedure of Example 2 gives the title compound.

EXAMPLE 56

7-[α-amino-α-(4'-carboxymethylthiophenyl)actadmido)-3-methoxymethyl-3-cephem-4-carboxylic acid Acylation of 7-amino-3-methoxymethyl-3-cephem-4-carboxylic acid [J.Med.Chem.,14,113(1971)] with D-N-t-butoxycarbonyl-p-t-butoxycarbonylmethylthiop xylglycine according to the procedure of Example 2 gives the title compound.

EXAMPLE 57

An injectable pharmeceutical composition is formed by adding sterile water or sterile saline solution (2 ml) to 500 mg of 7-[α-amino-α-(4'-carboxymethylthiophenyl)acetamido]-3-(1-methyl-1,2,3,4-tetrazol-5-ylthiomethyl)-3-cephem-4-carboxylic acid, sodium salt.

Pharmaceutical compositions of the other antibacterial compounds within the scope of Formula I or disclosed above may be formulated in a similar manner.

EXAMPLE 58

7-[D-α-Amino-α-(4'-carboxymethylaminophenyl)acetamido]-3-(1-methyl-1,2,3,4-tetrazol-5-ylthiomethyl)-3-cephem-4-carboxylic acid (Compound No. 76746)

The title compound was obtained from 1.15 g (3.02 mmol) of D-N-t-butoxycarbonyl-p-t-butoxycarbonylmethylainophenylglycine, 1,16 g (3.02 mmol) of 7-amino-3-(1-methyl-1,2,3,4-tetrazol-5-ylthiomethyl)-3-cephem-4-carboxylic acid t-butyl ester and 0.640 g (3.02 mmol) of dicyclohexylcarbodiimide in dry methylene chloride by the procedure described in Example 6. The initial reaction mixture was stirred at 0° for 1 hour then at 25° for 2 hours. Before deblocking, the intermediate was purified by chromatography on silica gel with ethyl acetate-benzene. Deblocking was accomplished by the procedure described in Example 28.

| Analysis of salt: $C_{20}H_{22}N_8O_6S_2$ . ⅓ $CF_3COOH$ . ⅔ $H_2O$ (605.099) | | |
|---|---|---|
| | Theory | Found |
| C | 41.68 | 41.70 |
| H | 4.00 | 4.12 |
| N | 18.52 | 18.33 |

The salt is converted to the zwitterion as in Example 6.

EXAMPLE 59

D-N-t-Butoxycarbonyl-p-carbamylmethylaminophenyl-glycine

A solution of 2.84 g (0.01 mol) of D-N-t-butoxycarbonyl-p-aminophenylglycine hydrate, 2.84 g (0.22 mol) of N,N-diisopropylethylamine and 2.22 g (0.012 mol) of α-idioacetamide in 50 ml of absolute alcohol was refluxed for three hours. The reaction mixture was concentrated in vacuo, the residue was dissolved in water and the solution brought to pH 8.5 with 5% sodium bicarbonate and washed with ethyl acetate. More ethyl acetate was added, the pH was adjusted to 1.5 with 3N hydrochloric acid and the layers were separated. The organic phase was washed ($H_2O$), dried ($MgSO_4$) and concentrated to give the title compound. D-p-carbamylmethylaminophenylglycine is obtained as its salt from treatment of the title compound with trifluoroacetic acid as described in Exaple 1.

EXAMPLE 60

7-[D-α-Amino-α-(4'-carbamylmethylainomethyl)acetamido]-3-(5-methyl-1,3,4-thiadiazol-2-ylthiomethyl)-3-cephem-4-carboxylic acid (Compound No. 72546)

To a mixture of 1.00 g (2.5 mmol) of 7-amino-3-(5-methyl-1,3,4-thiadiazol-2-ylthiomethyl)-3-cephem-4-carboxylic acid t-butyl ester and 0.81 g (2.5 mmol) of D-N-t-butoxycarbonyl--p-carbamylmethylaminophenylglycine in 10 ml of methylene chloride and 5 ml of dimethylformamide was added a solution of 0.515 g (2.5 mmol) of dicyclohexylcarbodiimide in 10 ml of methylene chloride. The reaction mixture was stirred at 25° for 2 hours, then it was filtered and the filtrate was washed with 3N hydrochloric acid, 5% sodium bicarbonate and water. After drying (MgSO₄), the solvent was removed in vacuo and the residue was dissolved in a small amount of chloroform, filtered and chromatographed on silica gel to give 7-[D-α-(t-butoxycarbonyl amino)-α-(4'-carbamylmethylaminophenyl)acetamido]-3-(5-methyl-1,3,4-thiadazol-2-ylthiomethyl)-3-cephem-4-carboxylic acid t-butyl ester. Deblocking was accomplished by stirring a solution of the intermediate in 10 ml of cold trifluoroacetic acid and 2 ml of anisole at 25° for 2 hours as previously described to give the salt of the title compound. The zwitterion is obtained from the trifluoroacetate salt as in Example 6.

I claim:
1. A compound of the formula:

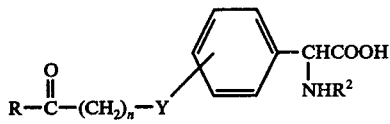

in which:
Y is O or NH;
$n$ is 1 to 5;
R is OR', where R' is lower alkyl of from one to four carbon atoms; and
$R^2$ is hydrogen.
2. A compound as claimed in claim 1 where $n$ is 1 or 2.
3. A compound as claimed in claim 1, being the compound p-carbomethoxymethoxyphenylglycine.
4. A compound as claimed in claim 1, being the compound p-carbomethoxymethylaminophenylglycine.

* * * * *